(12) United States Patent
Ogawa

(10) Patent No.: US 11,408,824 B2
(45) Date of Patent: Aug. 9, 2022

(54) BIOLOGICAL MATERIAL MEASUREMENT DEVICE

(71) Applicant: MITSUBISHI ELECTRIC CORPORATION, Chiyoda-ku (JP)

(72) Inventor: Shimpei Ogawa, Chiyoda-ku (JP)

(73) Assignee: MITSUBISHI ELECTRIC CORPORATION, Tokyo (JP)

(*) Notice: Subject to any disclaimer, the term of this patent is extended or adjusted under 35 U.S.C. 154(b) by 64 days.

(21) Appl. No.: 16/961,847

(22) PCT Filed: Oct. 29, 2018

(86) PCT No.: PCT/JP2018/040072
§ 371 (c)(1),
(2) Date: Jul. 13, 2020

(87) PCT Pub. No.: WO2019/176157
PCT Pub. Date: Sep. 19, 2019

(65) Prior Publication Data
US 2020/0408686 A1    Dec. 31, 2020

(30) Foreign Application Priority Data
Mar. 15, 2018    (JP) .............................. JP2018-048332

(51) Int. Cl.
*G01N 21/63* (2006.01)
*G01N 33/483* (2006.01)
(Continued)

(52) U.S. Cl.
CPC ........... *G01N 21/63* (2013.01); *G01N 33/483* (2013.01); *G01N 21/552* (2013.01); *G01N 33/66* (2013.01)

(58) Field of Classification Search
CPC .............. G01N 21/553; G01N 21/648; G01N 33/54373; G01N 21/658; G01N 21/554;
(Continued)

(56) References Cited

U.S. PATENT DOCUMENTS

| | | | |
|---|---|---|---|
| 6,628,376 B1 * | 9/2003 | Nikitin | G01N 21/553 356/38 |
| 8,836,948 B2 * | 9/2014 | Liu | G01B 11/2441 356/450 |

(Continued)

FOREIGN PATENT DOCUMENTS

| | | | | |
|---|---|---|---|---|
| CN | 1293757 A | * | 5/2001 | ....... G01N 33/54373 |
| DE | 10316514 A1 | * | 2/2004 | ......... G01N 21/3563 |

(Continued)

OTHER PUBLICATIONS

Jiang, L. et al., "Multifunctional Hyperbolic Nanogroove Metasurface for Submolecular Detection," Small, Jun. 2017, vol. 13, 17006000, pp. 1-8, supporting information, pp. 1-10.

(Continued)

*Primary Examiner* — Michael P Stafira
(74) *Attorney, Agent, or Firm* — Xsensus LLP

(57) ABSTRACT

A biological material measurement device 80 comprises; a first light source emitting a first light; an ATR prism 20 including a front surface and a back surface and allowing the first light made incident from one end to be transmitted therethrough and emitted from the other end; a hyperbolic metamaterial layer 90 including a front surface and a back surface and arranged on the front surface of the ATR prism 20 such that the back surface of the hyperbolic metamaterial layer is in contact therewith; and a first light detector detecting the first light emitted from the ATR prism 20. An amount of a biological material in a living body is measured from the detected first light.

20 Claims, 11 Drawing Sheets

(51) Int. Cl.
*G01N 21/552* (2014.01)
*G01N 33/66* (2006.01)

(58) Field of Classification Search
CPC .. G01N 21/6428; G01N 21/552; G01N 21/05; G01N 2021/0346; G01N 21/645; G01N 21/03; G01N 21/253; G01N 21/64; G01N 2021/6439; G01N 21/41; G01N 21/7703; G01N 2021/7786; G01N 21/7743; G01N 2021/6463; G01N 21/6456; G01N 2021/6441; G01N 21/77; G01N 2201/06113; G01N 21/0303; G01N 21/75; G01N 21/6452; G01N 2021/7776; G01N 2021/6434; G01N 2021/757; G01N 21/6454; G01N 2201/067; G01N 2201/068; G01N 2201/08; G01N 21/00; G01N 21/27; G01N 21/65; G01N 21/774; G01N 33/483; G01N 33/54393; G01N 2021/7773; G01N 21/211; G01N 21/33; G01N 21/3563; G01N 21/43; G01N 21/4788; G01N 33/543; G01N 33/54353; G01N 2021/5957; G01N 21/17; G01N 21/51; G01N 2201/12; G01N 33/54326; G01N 2021/258; G01N 2021/8528; G01N 21/0332; G01N 21/35; G01N 21/3577; G01N 21/7746; G01N 21/8507; G01N 33/553; G01N 2021/212; G01N 2021/651; G01N 21/25; G01N 21/4133; G01N 21/45; G01N 2201/0221; G01N 33/56983; G01N 21/47; G01N 21/63; G01N 2201/061; G01N 2201/0612; G01N 2201/0627; G01N 2201/1217; G01N 2201/126; G01N 29/00; G01N 33/442; G01N 33/48; G01N 33/54386; G01N 33/66; G01N 1/10; G01N 2021/054; G01N 2021/414; G01N 2021/436; G01N 2021/437; G01N 2021/6432; G01N 21/431; G01N 21/6408; G01N 21/6458; G01N 21/69; G01N 21/76; G01N 21/78; G01N 2201/1056; G01N 33/50; G01N 33/54366; G01N 33/57488; G01N 2021/6423; G01N 2021/7716; G01N 21/1717; G01N 21/272; G01N 21/31; G01N 21/359; G01N 21/49; G01N 21/643; G01N 21/6486; G01N 27/42; G01N 33/227; G01N 33/542; G01N 33/544; G01N 33/548; G01N 33/551; G01N 33/6857; G01N 11/167; G01N 15/0606; G01N 2015/0046; G01N 2015/0693; G01N 2021/0325; G01N 2021/1725; G01N 2021/3595; G01N 2021/558; G01N 2021/646; G01N 2021/6469; G01N 2021/8825; G01N 21/3504; G01N 21/55; G01N 21/636; G01N 21/783; G01N 21/8422; G01N 21/85; G01N 21/94; G01N 21/9501; G01N 21/9503; G01N 21/956; G01N 2333/11; G01N 2800/52; G01N 33/005; G01N 33/54346; G01N 33/582; G01N 33/6854; G01N 37/00; G01N 5/00; G01N 9/002

See application file for complete search history.

(56) References Cited

U.S. PATENT DOCUMENTS

| | | | |
|---|---|---|---|
| 2016/0170098 A1 | | 6/2016 | Ivanovich et al. |
| 2017/0215796 A1 | | 8/2017 | Giebeler et al. |
| 2017/0316487 A1 | * | 11/2017 | Mazed ............... G06Q 30/0241 |

FOREIGN PATENT DOCUMENTS

| | | | | | |
|---|---|---|---|---|---|
| DE | 102014108424 B3 | * | 6/2015 | ......... | A61B 5/14532 |
| EP | 0534083 A2 | * | 3/1993 | ............ | G02F 1/195 |
| JP | H07174693 A | * | 7/1995 | | |
| JP | 2004085262 A | * | 3/2004 | | |
| JP | 2012-70907 A | | 4/2012 | | |
| JP | 2013024606 A | * | 2/2013 | | |
| JP | 2014-224810 A | | 12/2014 | | |
| JP | 2015078904 A | * | 4/2015 | | |
| JP | 2017-531808 A | | 10/2017 | | |
| JP | 2017219512 A | * | 12/2017 | | |
| JP | 2018028467 A | * | 2/2018 | | |
| JP | 2018205156 A | * | 12/2018 | | |
| WO | WO-0188509 A1 | * | 11/2001 | ........... | G01N 21/553 |
| WO | WO-03083458 A2 | * | 10/2003 | ............ | G01N 21/85 |
| WO | WO-2017038714 A1 | * | 3/2017 | ......... | G01N 21/3586 |
| WO | WO-2018012436 A1 | * | 1/2018 | ........... | G01N 21/648 |

OTHER PUBLICATIONS

Smolyaninov, I. I. et al., "Hyperbolic metamaterials: Novel physics and applications," Solid-State Electronics, Jun. 2017, vol. 136, pp. 102-112.
Saleki, Z. et al., "Optical properties of a one-dimensional photonic crystal containing a graphene-based hyperbolic metamaterial defect layer," Applied Optics, Jan. 2017, vol. 56, No. 2, pp. 317-323.
International Search Report dated Jan. 22, 2019 in PCT/JP2018/040072 filed on Oct. 29, 2018, 2 pages.
Office Action dated Mar. 15, 2021, in corresponding Indian patent Application No. 202027038791, 6 pages.

* cited by examiner

96

96

96

BIOLOGICAL MATERIAL MEASUREMENT DEVICE

TECHNICAL FIELD

The present invention relates to a biological material measurement device and, more particularly, to a biological material measurement device measuring a biological material such as sugar existing in a living body by using an infrared light.

BACKGROUND ART

Biological material measurement devices measuring components of material in a living body such as blood sugar include invasive devices using puncture or blood collection and non-invasive devices not using puncture or blood collection. A blood sugar level measurement device (blood sugar level sensor) used on a daily basis is desirably a non-invasive measurement device because of alleviation of patient discomfort. A non-invasive blood sugar level measurement device is possibly a sensor using an infrared light enabling detection of a fingerprint spectrum of sugar. For example, Patent Document 1 discloses a blood sugar level sensor reflecting an infrared light multiple times in a prism to improve an attenuation rate of infrared light due to surface plasmon resonance and thereby improving the sensitivity of the sensor (see, e.g., [0057]).

PRIOR ART DOCUMENT

Patent Document

Patent Document 1: Japanese Laid-Open Patent Publication No. 2012-070907

SUMMARY OF THE INVENTION

Problem to be Solved by the Invention

However, infrared light is absorbed in a large amount by water in the skin and therefore can only reach a skin surface. Therefore, in the conventional technique, the effect of infrared light absorption by sugar such as glucose inside the skin cannot significantly be distinguished from the effect of infrared light absorption by water, and a good signal-to-noise ratio (SN ratio) cannot be obtained. Therefore, the blood sugar level cannot stably and accurately be measured.

Therefore, an object of the present invention is to provide a non-invasive biological material measurement device capable of stably and accurately measuring an amount of a biological material.

Means for Solving Problem

An aspect of the present invention provides a biological material measurement device comprising: a first light source emitting a first light; an ATR prism including a front surface and a back surface and allowing the first light made incident from one end to be transmitted therethrough and emitted from the other end; a hyperbolic metamaterial layer including a front surface and a back surface and arranged on the front surface of the ATR prism such that the back surface of the hyperbolic metamaterial layer is in contact therewith; and a first light detector detecting the first light emitted from the ATR prism, wherein an amount of a biological material in a living body is measured from the detected first light.

Effect of the Invention

The present invention can provide the non-invasive biological material measurement device capable of stably and accurately measuring an amount of a biological material.

BRIEF DESCRIPTION OF DRAWINGS

FIG. 5b is a perspective view showing the hyperbolic metamaterial of FIG. 5a.

MODES FOR CARRYING OUT THE INVENTION

Figure 1:
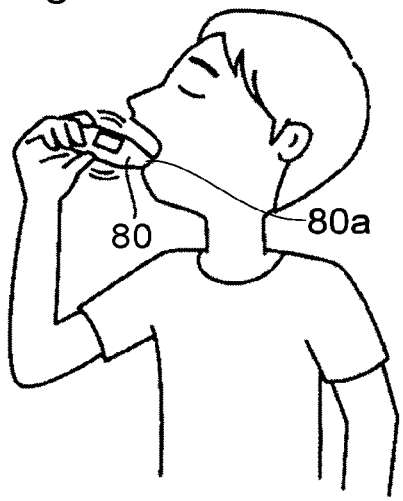
FIG. 1 is a schematic diagram showing an example of use of a non-invasive blood sugar level measurement device according to a first embodiment of the present invention.

A biological material measurement device according to an embodiment of the present invention will now be described with reference to the drawings. In each embodiment, the same constituent elements are denoted by the same reference numerals and will not be described.

First Embodiment

FIG. 1 is a schematic diagram showing an example of use of a non-invasive blood sugar level measurement device generally denoted by 80 according to a first embodiment of the present invention. A head (distal end) 80a of the non-invasive blood sugar level measurement device 80 is brought into contact with a skin of a subject to measure a blood sugar level of the subject. The skin brought into contact with the head 80a of the non-invasive blood sugar level measurement device 80 is desirably a lip with thin keratin; however, the present invention is not limited thereto, and the skin may be that of a cheek, an earlobe, or a back of a hand, for example.

Figure 2:
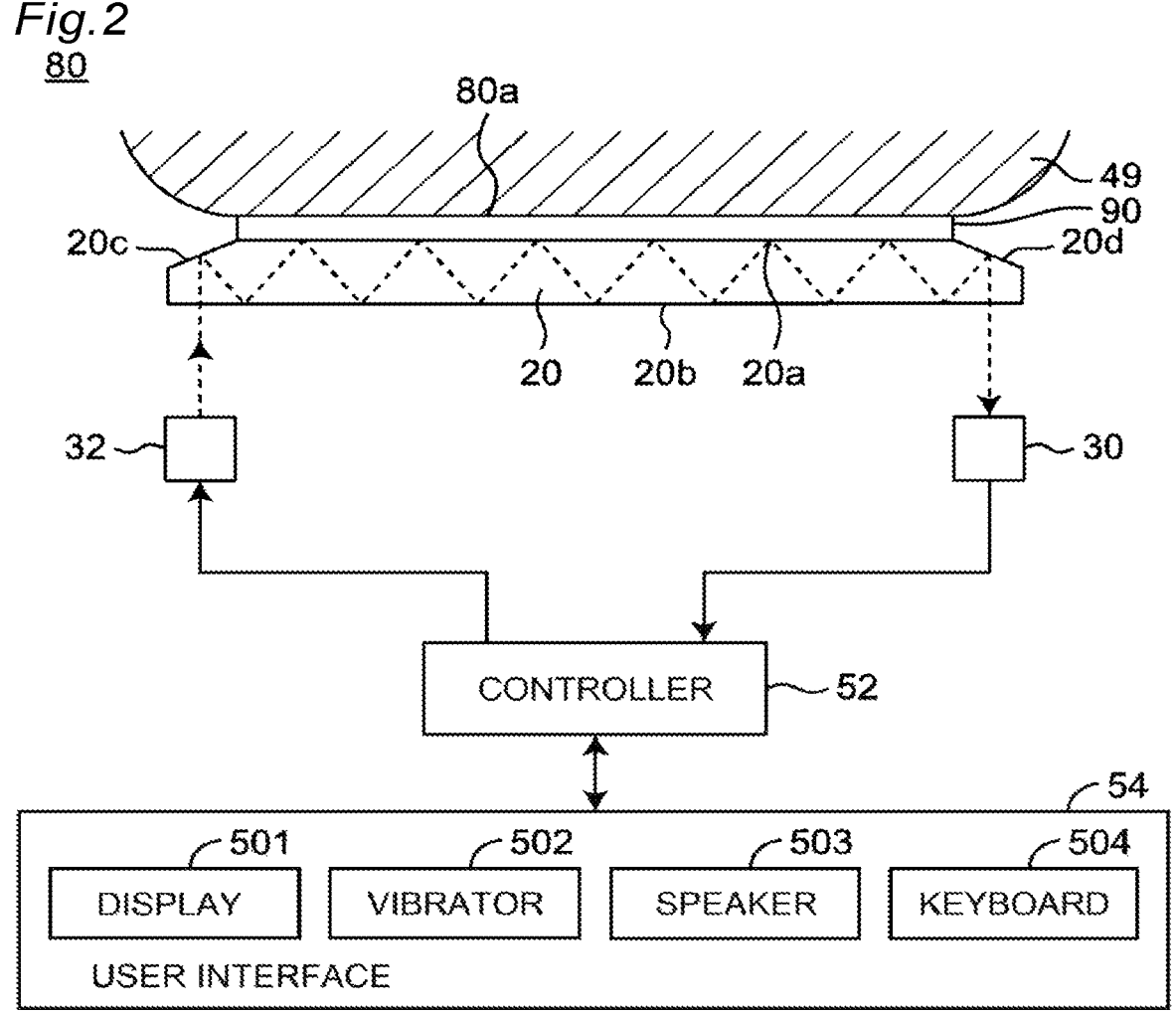
FIG. 2 is a schematic diagram showing a configuration of the non-invasive blood sugar level measurement device according to the first embodiment of the present invention.

FIG. 2 is a schematic diagram showing a configuration of the non-invasive blood sugar level measurement device 80 according to the first embodiment of the present invention. The non-invasive blood sugar level measurement device 80 includes an infrared light source 32 emitting an infrared light having a whole or a part of an absorption wavelength region of a biological material (8.5 µm to 10 µm), an ATR prism 20 through which the infrared light emitted from the infrared light source 32 is transmitted, and an infrared light detector 30 detecting the intensity of the infrared light emitted from the ATR prism 20. The non-invasive blood sugar level measurement device 80 further includes a hyperbolic metamaterial 90 formed on the head 80a of the non-invasive blood sugar level measurement device 80. In other words, the hyperbolic metamaterial 90 is formed on the ATR prism 20.

The infrared light source 32 is a quantum cascade laser module, for example. The quantum cascade laser is a single light source and has a large output and a high SN ratio, therefore enabling highly accurate measurement. The quantum cascade laser module is equipped with a lens for collimating a beam.

The infrared light emitted from the infrared light source 32 is incident on the ATR prism 20. The incident infrared light is transmitted through the ATR prism 20 while being repeatedly totally reflected and is subsequently emitted from the ATR prism 20. Therefore, schematically, the infrared light emitted from the infrared light source 32 is reflected by an end surface 20c of the ATR prism 20. The reflected infrared light is transmitted inside the ATR prism 20 and reflected by an end surface 20b, is then transmitted inside the ATR prism 20 to reach an end surface 20a, is transmitted through the hyperbolic metamaterial 90 and reflected by a surface (distal end surface) of the hyperbolic metamaterial 90 in contact with a skin 49 of the subject, and is then transmitted inside the hyperbolic metamaterial 90 and inside the ATR prism 20 and reflected by the end surface 20b of the ATR prism 20 again. The infrared light is repeatedly reflected by the surface of the hyperbolic metamaterial 90 and reflected by the end surface 20b of the ATR prism 20 to reach the end surface 20d of the ATR prism 20 and is reflected there and emitted from the ATR prism 20.

An anti-reflection coating may be applied to a portion of the ATR prism 20 where the infrared light is emitted. Alternatively, the infrared light emitted from the infrared light source 32 may be p-polarized light, and the ATR prism 20 may be processed such that the incident angle and the emission angle of the infrared light achieve Brewster's angle.

For example, the material of the ATR prism 20 is a single crystal of zinc sulfide (ZnS) transparent to light having a wavelength in a mid-infrared region and having a relatively small refractive index. The material of the ATR prism 20 may be a known material such as zinc selenide (ZnSe). However, the material of the ATR prism 20 is not limited thereto.

A portion of the ATR prism 20 or the hyperbolic metamaterial 90 coming into contact with the skin 49 may be coated with a thin film containing $SiO_2$ or SiN so as not to cause harm to the human body.

The infrared light emitted from the ATR prism 20 enters the infrared light detector 30. The infrared light detector 30 is a module equipped with a MEMS (Micro Electro Mechanical Systems) measurement device or an uncooled measurement device such as a thermopile, for example. The infrared light detector 30 includes an electric circuit such as a preamplifier and a lens for collecting the infrared light incident on the infrared light detector 30 to an element of the measurement device. Further details of the infrared light detector 30 will be described later.

The non-invasive blood sugar level measurement device 80 further includes a controller 52 electrically connected to the infrared light source 32 and the infrared light detector 30. The controller 52 can control the oscillation of the infrared light source 32, the wavelength and the intensity of the infrared light emitted from the infrared light source 32, etc. The controller 52 receives intensity data of the detected infrared light from the infrared light detector 30 and calculates a blood sugar concentration in a living body based thereon.

The non-invasive blood sugar level measurement device 80 further includes a user interface 54 electrically connected to the controller. For example, the user interface 54 includes a display 501 displaying measurement start means, measurement condition setting means, etc. to a user, a vibrator 502 and a speaker 503 notifying the user of a measurement status (e.g., measurement start and completion) with vibration and voice, respectively, and a keyboard 504 for the user performing a measurement start operation, a measurement condition setting operation, etc.

Figure 3:
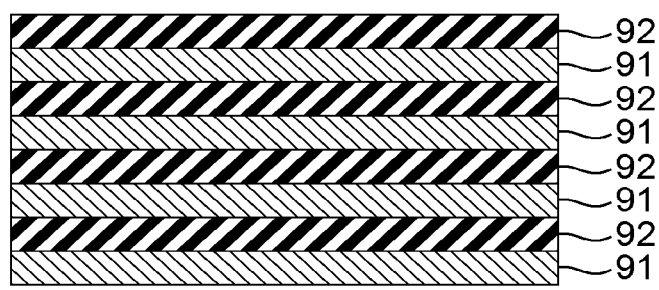
FIG. 3 is a schematic cross-sectional view of an example of a hyperbolic metamaterial of the non-invasive blood sugar level measurement device according to the first embodiment of the present invention.

FIG. 3 shows a schematic cross-sectional view of an example of the hyperbolic metamaterial 90. The hyperbolic metamaterial 90 has a multilayer structure in which metal layers 91 and dielectric layers 92 are alternately laminated. The metal layers 91 and the dielectric layers 92 desirably have a thickness less than ¼ of a wavelength used. For example, when an infrared light is used for detecting sugar, the thickness of each of the metal layers 91 and the dielectric layers 92 is about 10 nm. In FIG. 3, the hyperbolic metamaterial 90 has an eight-layer structure; however, the number of layers is not limited thereto.

The metal layers 91 of the hyperbolic metamaterial 90 are made of a material generating surface plasmon in the wavelength region of the light used. In the non-invasive blood sugar level measurement device 80 using the wavelength of infrared light for detecting a biological material such as sugar, the metal layers 91 of the hyperbolic metamaterial 90 are made of gold or silver, for example. The metal layers 91 of the hyperbolic metamaterial 90 may be layers made of a compound such as titanium nitride or graphene. Particularly, when infrared light is used, graphene is a material with a low optical loss and is therefore advantageous. Alternatively, the metal layers 91 of the hyperbolic metamaterial 90 may be layers made of a semiconductor material. The semiconductor material is advantageous since desired physical properties can be obtained by adjusting a doping concentration.

The dielectric layers 92 of the hyperbolic metamaterial 90 are preferably made of silicon oxide ($SiO_2$), silicon nitride (SiN), aluminum oxide ($Al_2O_3$), or magnesium fluoride ($MgF_2$); however, the present invention is not limited thereto.

Figure 4:
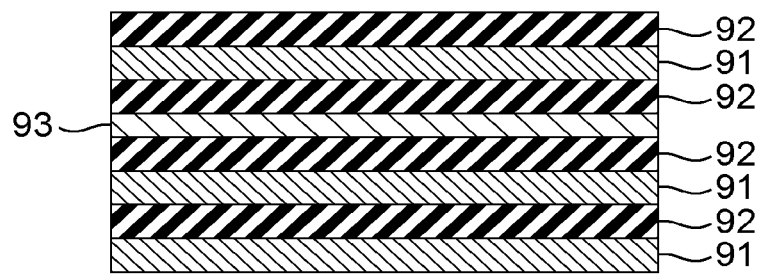
FIG. 4 is a schematic cross-sectional view of another example of the hyperbolic metamaterial of the non-invasive blood sugar level measurement device according to the first embodiment of the present invention.

FIG. 4 is a schematic cross-sectional view showing another example of the hyperbolic metamaterial denoted by reference numeral 95. The hyperbolic metamaterial 95 includes at least one defect layer 93 in a laminated structure of the metal layers 91 and the dielectric layers 92. As used herein, "defect" means being different from surrounding regularity. The thickness of the defect layer 93 is different from the thicknesses of the metal layers 91 and the dielectric layers 92. The defect layer 93 is a metal layer or a dielectric layer.

In the periodic laminated structure of the hyperbolic metamaterial, a functional wavelength region can be designed by adjusting the number of layers, the layer thickness, the materials, etc. By introducing the defect layer 93 disturbing the periodicity into the periodic laminated structure, a light having a certain wavelength can be confined in the defect layer 93, or transmittance of a light having a certain wavelength can be improved. For example, while the infrared light having a wavelength absorbed by a biological material such as glucose is directly transmitted, a dispersion relationship of the laminated structure can be used as a dispersion relationship of the hyperbolic metamaterial for visible light.

As described above, by introducing the defect layer 93, the dispersion relationship of the stacked structure can be controlled in accordance with a wavelength. Additionally, a degree of freedom of measurement can be improved. Therefore, the accuracy of measurement can be improved. In a second embodiment described below, the defect layer 93 may also be introduced and has the same effect as described above.

Figure 5A:
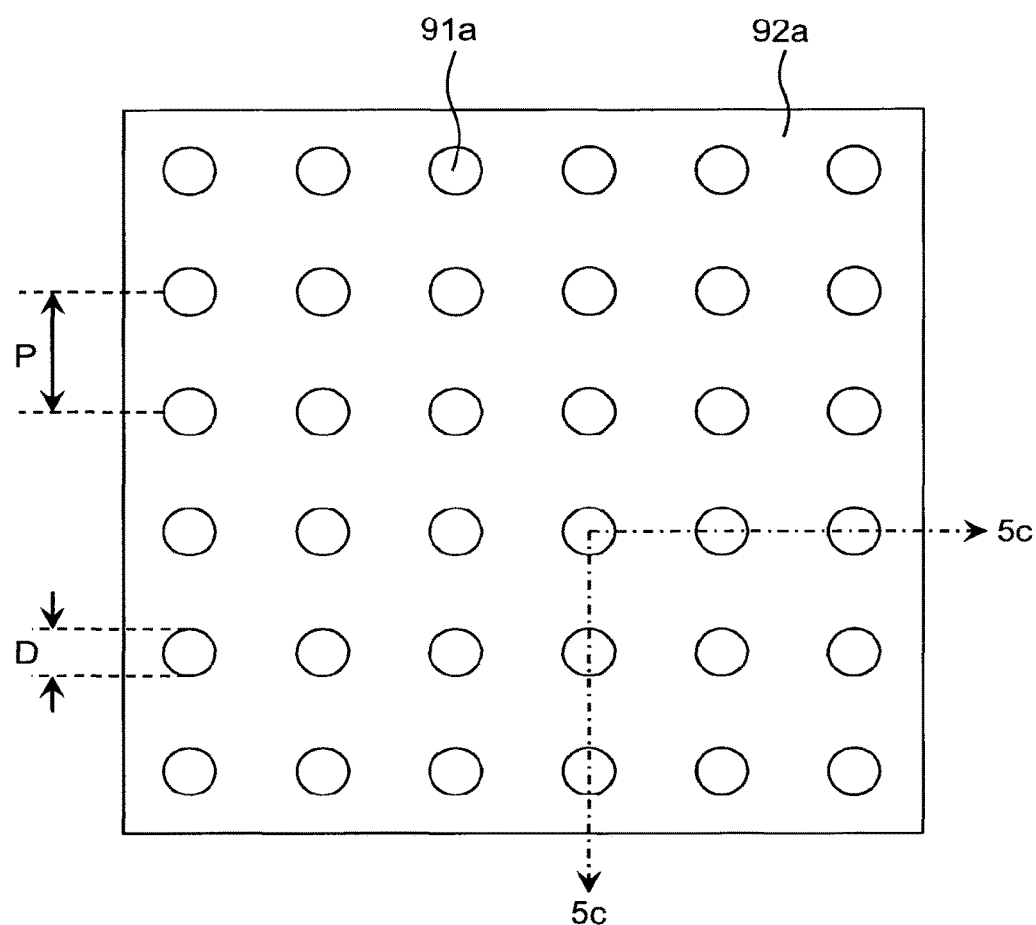
FIG. 5a is a schematic top view of yet another example of the hyperbolic metamaterial of the non-invasive blood sugar level measurement device according to the first embodiment of the present invention.
Figure 5B:
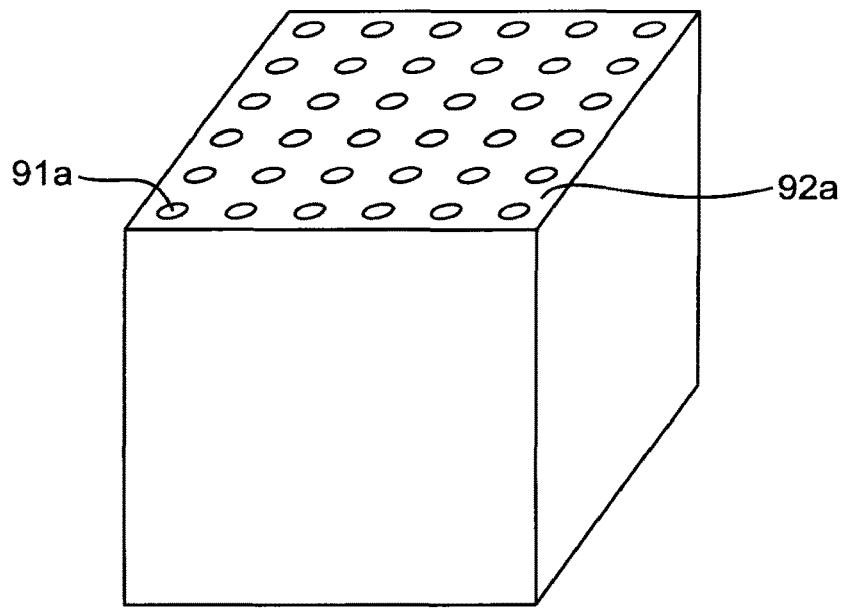
Figure 5C:
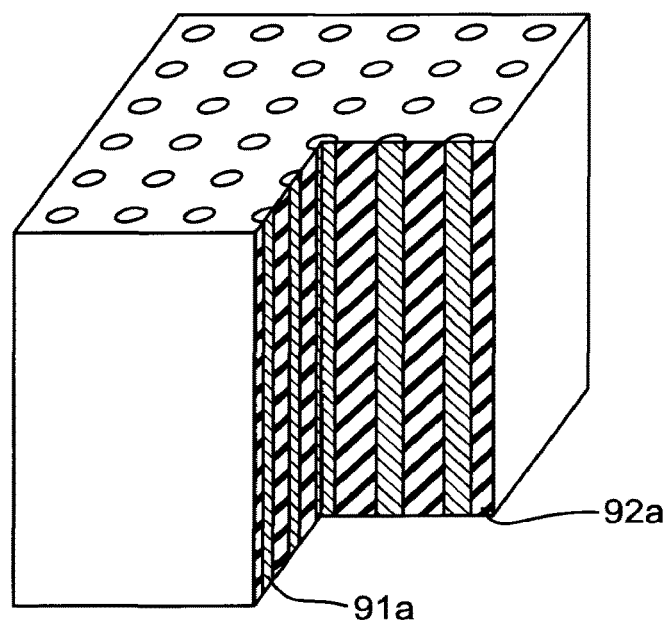
FIG. 5c is a partial cross-sectional perspective view of the hyperbolic metamaterial of FIG. 5b.

FIGS. 5a to 5c are diagrams showing another example of a hyperbolic metamaterial denoted by reference numeral 96. FIG. 5a is a top view of the hyperbolic metamaterial 96. FIG. 5b is a perspective view of the hyperbolic metamaterial 96. FIG. 5C is a partial cross-sectional perspective view showing a partial cross-section of the hyperbolic metamaterial 96 taken along a line 5c-5c of FIG. 5a.

The hyperbolic metamaterial 96 is made up of multiple metal rods 91a and a dielectric 92a filling a space around the metal rods 91a. In the example of FIGS. 5a to 5c, the metal rods 91a have a circular cylindrical shape with a bottom surface shape formed into a circle having a diameter D. Alternatively, the shape of the metal rods 91a is not limited to a circular cylindrical shape with a circular bottom surface shape and may be an elliptical cylindrical shape with an elliptical bottom surface shape or a quadrangular prism shape with a square or rectangular bottom surface shape as long as the characteristics of the hyperbolic metamaterial are satisfied. As shown in the top view of FIG. 5a, the metal rods 91a are two-dimensionally arranged in a radial direction in a period P in planar view. As with the metal layers 91 described above (see FIGS. 3 and 4), the metal rods 91a are made of a material generating surface plasmon in the wavelength region of the light used.

The thickness D and the period P of the metal rod 91a are desirably less than ¼ of the wavelength used. For example, when an infrared light is used for detecting sugar, the thickness and the period P of the metal rods 91a are each about 10 nm. FIGS. 5A to 5C merely show an example of arrangement of the metal rods 91a, and the arrangement of the metal rods 91a is not limited thereto.

Figure 6:
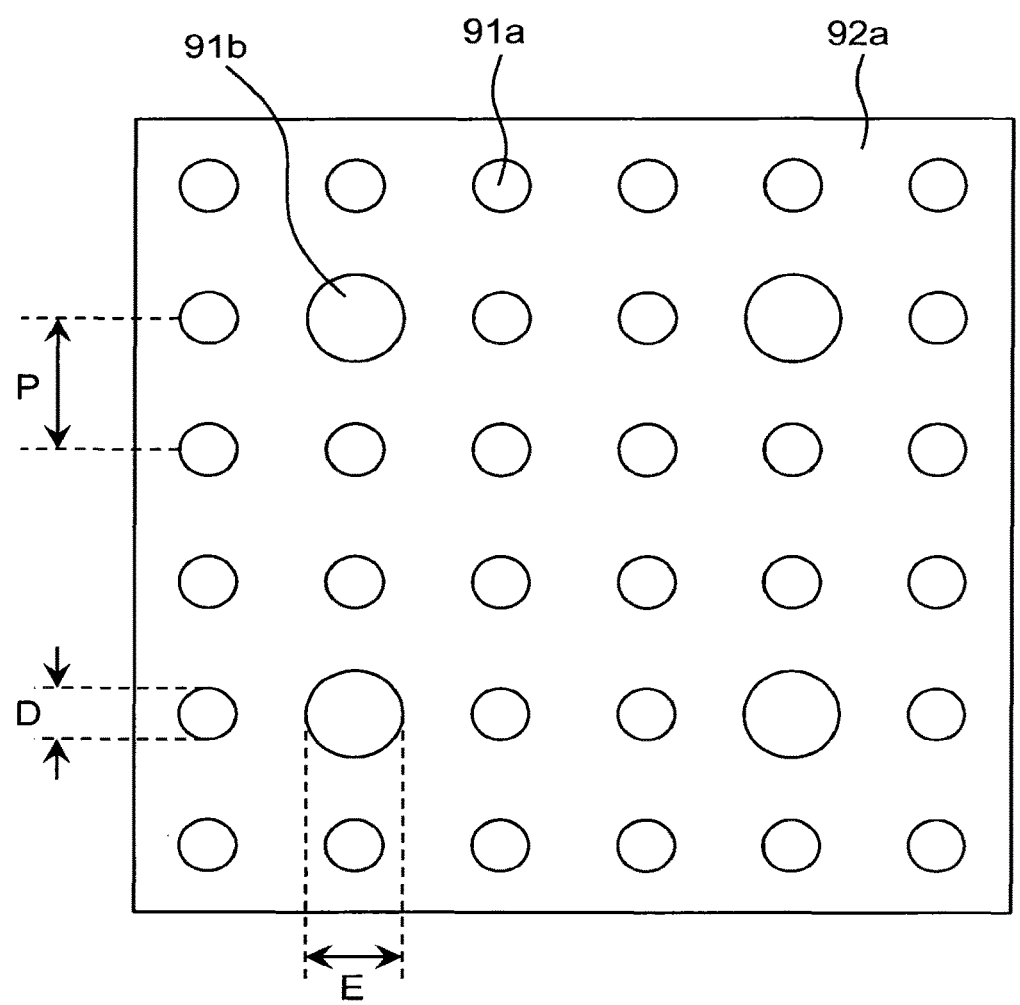
FIG. 6 is a schematic top view of still another example of the hyperbolic metamaterial of the non-invasive blood sugar level measurement device according to the first embodiment of the present invention.

FIG. 6 is a top view showing another example of a hyperbolic metamaterial denoted by reference numeral 97. In the periodic structure of the hyperbolic metamaterial, a functional wavelength region can be designed by adjusting the number, thickness, period, material, etc. of the metal rods 91a. The hyperbolic metamaterial 97 shown in FIG. 6 includes a defect rod 91b disturbing the regularity of size, period, etc. of the metal rods 91a. For example, the defect rod 91b is made of the same material as the metal rods 91a and has a thickness E different from the metal rods 91a. By introducing the defect rod 91b disturbing the regularity into the structure having the regularity as described above, a light having a specific wavelength can be confined around the defect rod 91b, or transmittance of a light having a certain wavelength can be improved.

In FIG. 6, a specific metal rod is selected from the metal rods 91a, and the thickness of the selected metal rod is increased to form the defect rod 91b as a defect region. The method of forming the defect region is not limited thereto, and the defect region may be formed by a method such as changing the shape of the metal rod 91a from a circular cylinder to a quadrangular prism, arranging a metal rod at a position disturbing the periodicity of arrangement of the metal rods 91a, or changing the material of the metal rod 91a, for example.

By introducing the defect rod 91b as described above, for example, while the infrared light having a wavelength absorbed by a biological material such as glucose is directly transmitted, a dispersion relationship of the laminated structure can be used as a dispersion relationship of the hyperbolic metamaterial for visible light.

The principle of blood sugar measurement by the non-invasive blood sugar level measurement device 80 will be described. When an infrared light is totally reflected at an interface between the ATR prism 20 and the hyperbolic metamaterial 90 and/or at an interface between the hyperbolic metamaterial 90 and the skin 49, an evanescent wave is generated. This evanescent wave penetrates into the skin 49 and is absorbed by a biological material such as sugar in the living body of the subject. Since the evanescent wave is absorbed in this manner, the intensity of the infrared light is attenuated. If an amount of the biological material is large, the evanescent wave is more absorbed, so that the intensity of infrared light is further attenuated.

The skin 49 is made up of the epidermis near the surface and the dermis under the epidermis. The epidermis includes the stratum corneum, the stratum granulosum, the stratum spinosum, and the stratum basale in order from near the surface. The respective thicknesses are about 10 μm, several μm, 100 μm, and several μm. Cells are generated in the stratum basale, and the cells are stacked up into the stratum spinosum. Since water (tissue interstitial fluid) does not reach the stratum granulosum above the stratum spinosum, cells die out. In the stratum corneum above the stratum granulosum, dead cells are in a hardened state. Sugar and other biological materials are present in the tissue interstitial fluid in the epidermis. The tissue interstitial fluid increases from the stratum corneum to the stratum spinosum. Therefore, the degree of attenuation of the totally reflected infrared light also changes depending on a length of penetration of the evanescent wave into the skin.

The intensity of the evanescent wave exponentially attenuates from a reflecting surface toward the skin, and the length of penetration into the skin is about the wavelength of infrared light. Therefore, when the non-invasive blood sugar level measurement device 80 uses an infrared light having a wavelength of 8.5 μm to 10 μm absorbed by sugar, the sugar present from the skin surface to a position at a depth of 8.5 μm to 10 μm can be detected.

The characteristics of the hyperbolic metamaterial 90 will be described. First, properties of a flat thin film will generally be described. It is assumed that an x axis and a y axis are perpendicular to each other and a thin film extends in the x-y plane. A direction perpendicular to the x axis and the y axis is defined as a z direction. The wave numbers in the x-, y-, and z-axis directions are $k_x$, $k_y$, and $k_z$, respectively. A dielectric constant ε and a magnetic permeability μ can be written as follows.

[Math. 1]

$$\varepsilon = \begin{pmatrix} \varepsilon_{xx} & 0 & 0 \\ 0 & \varepsilon_{yy} & 0 \\ 0 & 0 & \varepsilon_{zz} \end{pmatrix} \quad (1)$$

[Math. 2]

$$\varepsilon = \begin{pmatrix} \mu_{xx} & 0 & 0 \\ 0 & \mu_{yy} & 0 \\ 0 & 0 & \mu_{zz} \end{pmatrix} \quad (2)$$

If the material of the thin film is uniaxial crystal (i.e., in the case of $\varepsilon_{xx}=\varepsilon_{yy}\not\equiv\varepsilon_{zz}$), this can be written as $\varepsilon_{xx}=\varepsilon_{yy}\equiv\varepsilon_\perp$, $\varepsilon_{zz}\equiv\varepsilon_\parallel$, $\mu_{xx}=\mu_{yy}\equiv\mu_\perp$, $\mu_{zz}\equiv\mu_\parallel$, and therefore, the dielectric constant ε and the magnetic permeability μ can be written as Eqs (3) and (4), respectively.

[Math. 3]

$$\varepsilon = \begin{pmatrix} \varepsilon_\perp & 0 & 0 \\ 0 & \varepsilon_\perp & 0 \\ 0 & 0 & \varepsilon_\parallel \end{pmatrix} \quad (3)$$

[Math. 4]

$$\varepsilon = \begin{pmatrix} \mu_\perp & 0 & 0 \\ 0 & \mu_\perp & 0 \\ 0 & 0 & \mu_\parallel \end{pmatrix} \quad (4)$$

Generally, the dispersion relationship of light is represented by Eq. (5) below.

[Math. 5]

$$\frac{k_x^2+k_z^2}{\varepsilon_\parallel}+\frac{k_y^2}{\varepsilon_\perp}=\left(\frac{\omega}{c}\right)^2 \quad (5)$$

where, ω is the frequency of light, and c is the speed of light.

For an ordinary material (i.e., a material that is not a hyperbolic metamaterial), the values of $\varepsilon_\parallel$ and $\varepsilon_\perp$ are equal and are positive values. Therefore, Eq. (6) is satisfied.

[Math. 6]

$$\varepsilon_\parallel=\varepsilon_\perp>0 \quad (6)$$

Figure 7:
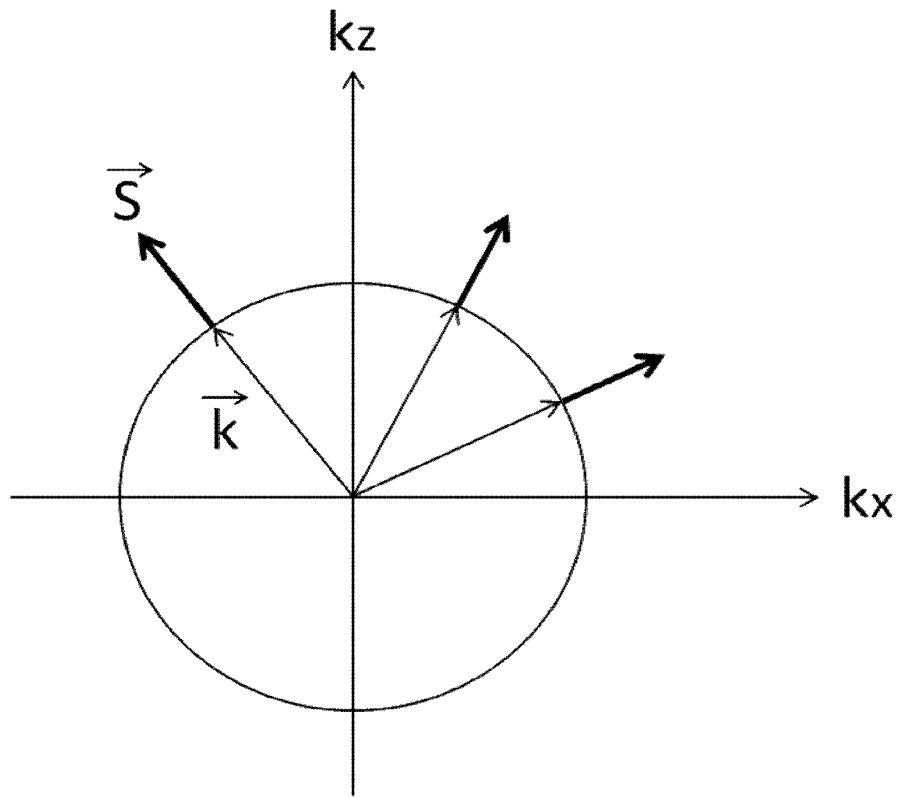
FIG. 7 is a diagram showing a dispersion relationship of an ordinary material when a vertical axis is $k_z$ and a horizontal axis is $k_x$.

FIG. 7 shows a dispersion relationship of an ordinary material (i.e., a material that is not a hyperbolic metamaterial) when a vertical axis is $k_z$ and a horizontal axis is $k_x$. S in FIG. 7 represents a pointing vector. As shown, the dispersion relationship represented in the wavenumber space is a sphere and is closed.

In contrast to the ordinary material described above, an electrical hyperbolic metamaterial is a material satisfying Eqs. (7) and (8) or Eqs. (7) and (9) below.

[Math. 7]

$$\mu_\perp=\mu_\parallel>0 \quad (7)$$

[Math. 8]

$$\varepsilon_\parallel<0 \text{ and } \varepsilon_\perp>0 \quad (8)$$

[Math. 9]

$$\varepsilon_\parallel>0 \text{ and } \varepsilon_\perp<0 \quad (9)$$

Figure 8:
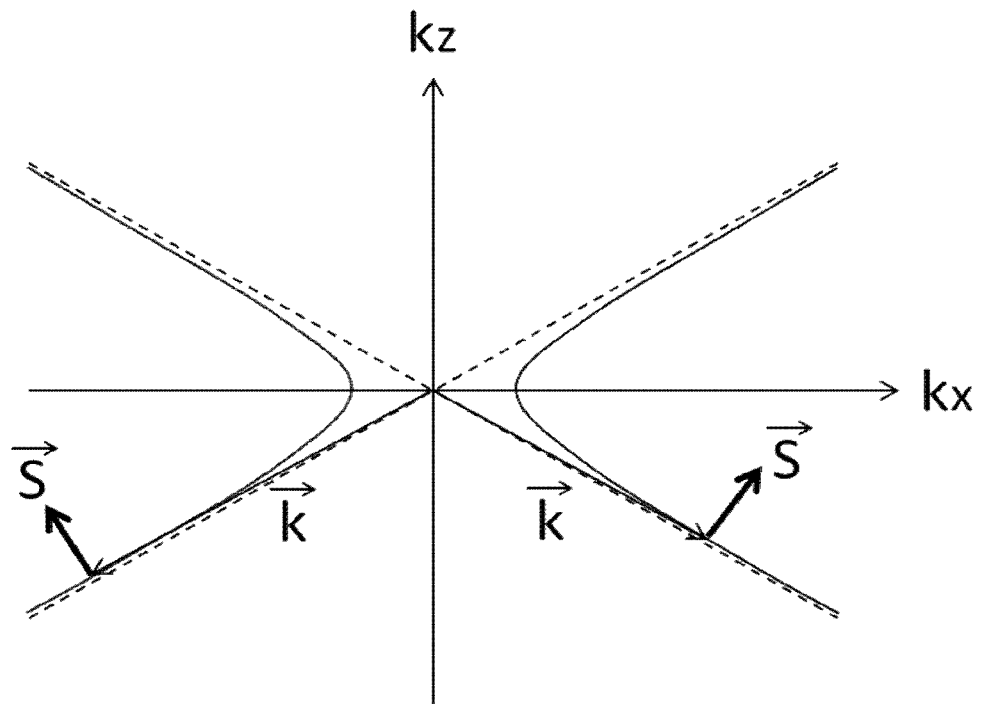
FIG. 8 is a diagram showing a dispersion relationship of the hyperbolic metamaterial when the vertical axis is $k_z$ and the horizontal axis is $k_x$.

Therefore, the dispersion relationship for the electrical hyperbolic metamaterial has a hyperbolic shape as shown in FIG. 8. Therefore, the wave number can be present regardless of how large it is. This means that the evanescent wave does not attenuate in the hyperbolic metamaterial.

Furthermore, in the non-invasive blood sugar level measurement device 80 according to the first embodiment of the present invention, a difference in refractive index can be reduced (the refractive indexes can be matched) between the skin 49 and the hyperbolic metamaterial 90 by adjusting the material and the thicknesses of the layers of the hyperbolic metamaterial 90 coming into contact with the skin 49. Therefore, when the non-invasive blood sugar level measurement device 80 according to the first embodiment of the present invention including the hyperbolic metamaterial 90 is used, the length of penetration of the evanescent wave into the skin 49 becomes longer as compared to a conventional blood sugar level sensor using surface plasmon. Therefore, the non-invasive blood sugar level measurement device 80 according to the first embodiment of the present invention can highly sensitively detect glucose in the skin.

The hyperbolas representative of the dispersion relationship of the hyperbolic metamaterial may not be separated as shown in FIG. 8 (see, e.g., "Poddubny, A.; Iorsh, I.; Belov, P.; Kivshar, Y. Hyperbolic metamaterials. Nature Photonics 2013, 7, 948-957").

Figure 9:
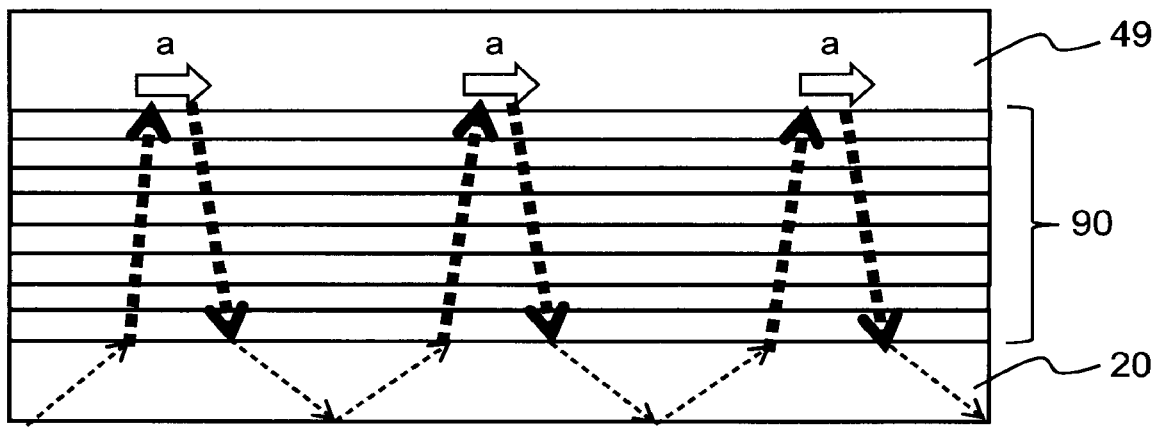
FIG. 9 is a schematic diagram showing optical paths of an infrared light and an evanescent wave traveling through an ATR prism, the hyperbolic metamaterial, and the skin.

FIG. 9 is a schematic diagram showing the optical paths of the infrared light and the evanescent wave traveling through the ATR prism 20, the hyperbolic metamaterial 90, and the skin 49. When the infrared light traveling through the ATR prism 20 reaches the interface between the ATR prism 20 and the hyperbolic metamaterial 90, the evanescent wave generated by the infrared light and/or the total reflection at the interface Propagates inside the hyperbolic metamaterial 90.

Whether only the infrared light, only the evanescent wave, or both of them penetrate into the hyperbolic metamaterial 90 can be selected by adjusting the layer thicknesses, the number of layers, the materials, etc. of the hyperbolic metamaterial 90.

As described above, since the length of penetration of the evanescent wave into the skin 49 becomes longer, a distance required for phase matching between an incident wave and a reflected wave increases (Goos-Hanchen shift, corresponding to a of FIG. 9).

Furthermore, in the hyperbolic metamaterial 90, the wavelength dependence of the light reflection angle becomes greater as compared to ordinary materials. Specifically, when the light having the wavelength to be measured and the light having the other wavelength are emitted from the hyperbolic metamaterial 90, a difference between the emission angle of the light having the wavelength to be measured and the light having the other wavelength is large as compared to when the lights are emitted from the ordinary materials. Therefore, if the infrared light detector 30 is disposed at the position of incidence of the light having the wavelength to be measured enters, the light having the other wavelength does not enter the infrared light detector 30, so that noises caused by the light having the other wavelength are not detected. Therefore, when the hyperbolic metamaterial 90 is used, the S/N ratio becomes favorable, and highly accurate measurement can be performed.

The hyperbolic metamaterial 90 can easily be manufactured by alternately laminating metal and insulating layers by sputtering. When graphene is adopted as the material of the metal layers 91 of the hyperbolic metamaterial 90, graphene formed by chemical vapor deposition on a copper foil is transferred onto an insulating film. Alternatively, graphene may be formed by screen printing, a solution coating method, etc.

Figure 10:
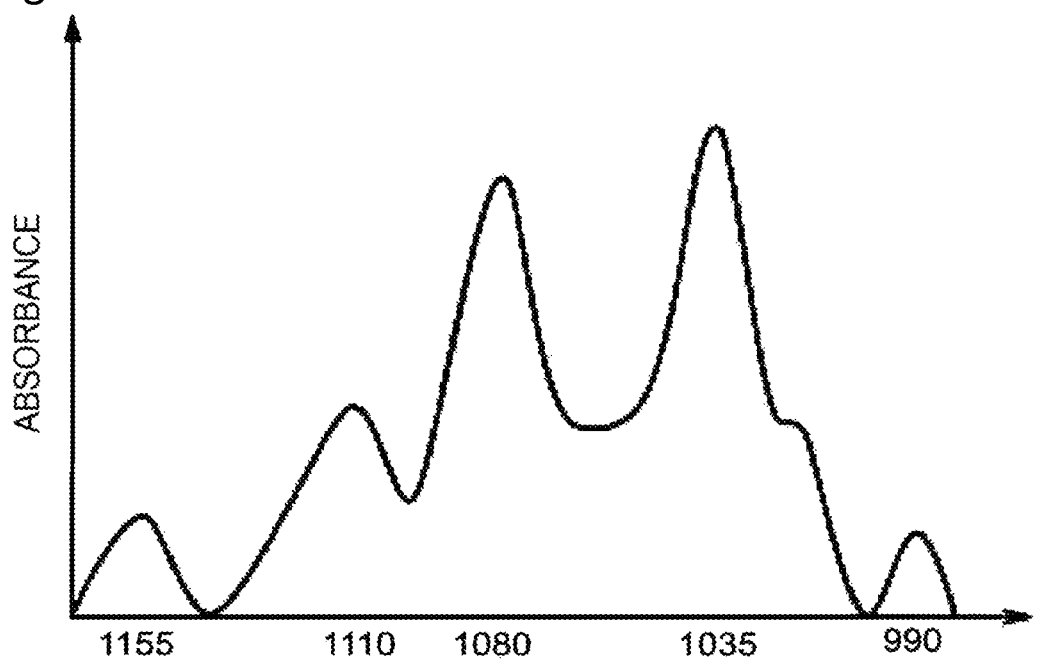
FIG. 10 is a diagram showing an infrared light absorption spectrum of sugar.

In the above description, the object to be measured by the non-invasive blood sugar level measurement device 80 according to the first embodiment of the present invention is a blood sugar level. FIG. 10 shows an infrared light absorption spectrum of sugar. However, the object to be measured is not limited to the blood sugar level and may be an amount of another biological material.

Although the non-invasive blood sugar level measurement device 80 uses infrared light has been described, the light used is not limited to infrared light. For example, the non-invasive blood sugar level measurement device 80 may use visible light or light having a wavelength in the THz region instead of infrared light.

As described above, by using the non-invasive blood sugar level measurement device 80 according to the first embodiment of the present invention, the length of penetration of the evanescent wave into the skin becomes longer as compared to conventional blood sugar level sensors, and the absorption of infrared light by biological materials in the skin increases. Additionally, the distance required for phase matching between the incident wave and the reflected wave (Goos-Hanchen shift) increases. Furthermore, the difference between the emission angle of the light having the wavelength to be measured and the emission angle of the light of the other wavelength is large, so that the light having the wavelength to be measured can be detected without detecting the light having the other wavelength, and high-precision measurement can be performed.

A configuration of the infrared light detector 30 included in the non-invasive blood sugar level measurement device 80 will be described in detail.

Figure 11:
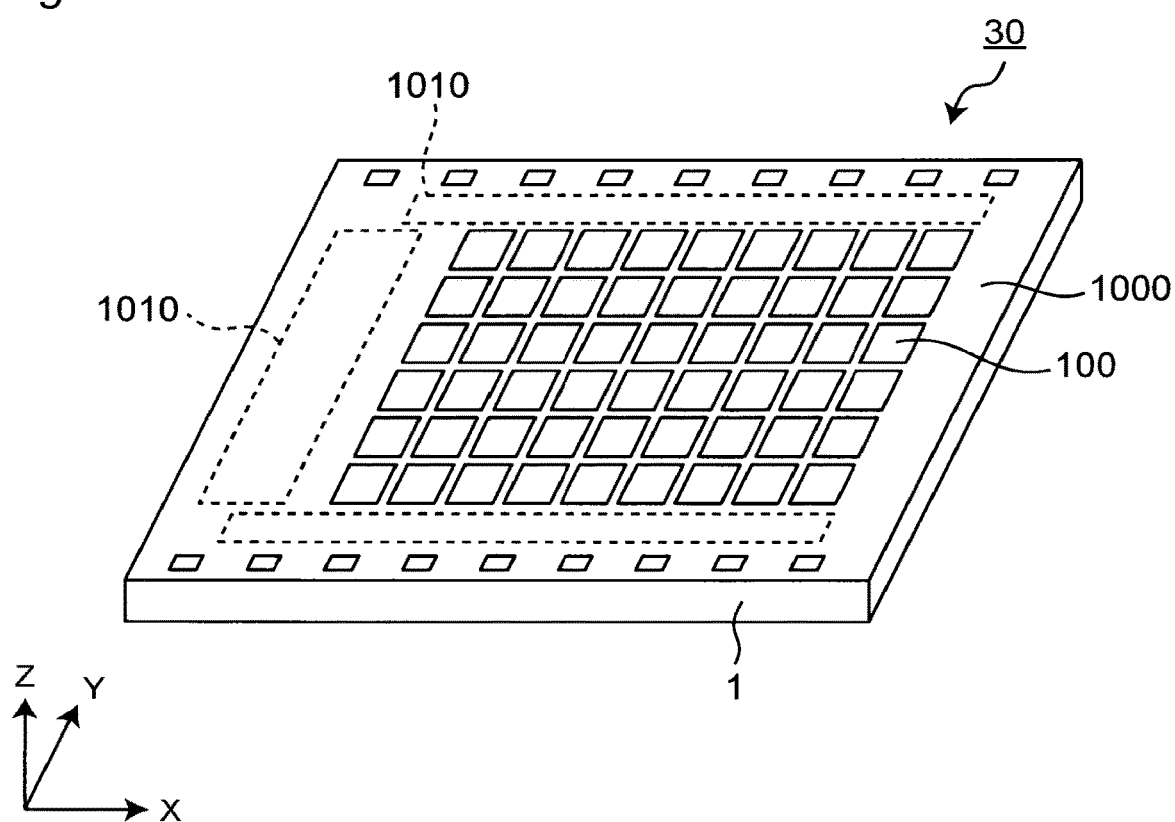
FIG. 11 is a perspective view showing a configuration example of an infrared light detector of the non-invasive blood sugar level measurement device according to the first embodiment of the present invention.

FIG. 11 is a perspective view showing a configuration example of the infrared light detector 30. For convenience of description, FIG. 11 shows an X axis, a Y axis perpendicular to the X axis, and a Z axis perpendicular to the X axis and the Y axis. The infrared light detector 30 includes a substrate 1 parallel to the X-Y plane, a sensor array 1000 arranged on the substrate, and a detection circuit 1010 arranged around the sensor array 1000. The sensor array 1000 includes multiple pixels (semiconductor optical elements) 100 arranged in a matrix shape (an array shape) in two directions (X and Y directions) orthogonal to each other. FIG. 11 shows the 54 (9×6) optical elements 100. The detection circuit 1010 processes signals detected by the optical elements 100. The detection circuit 1010 may detect an image by processing the signals detected by the optical elements 100. In the non-invasive blood sugar level measurement device 80, the infrared light detector 30 is arranged such that the infrared light enters the optical elements 100 of the sensor array 1000 vertically (in a direction parallel to the Z axis).

The optical elements 100 are thermal infrared sensors, for example.

Figure 12:
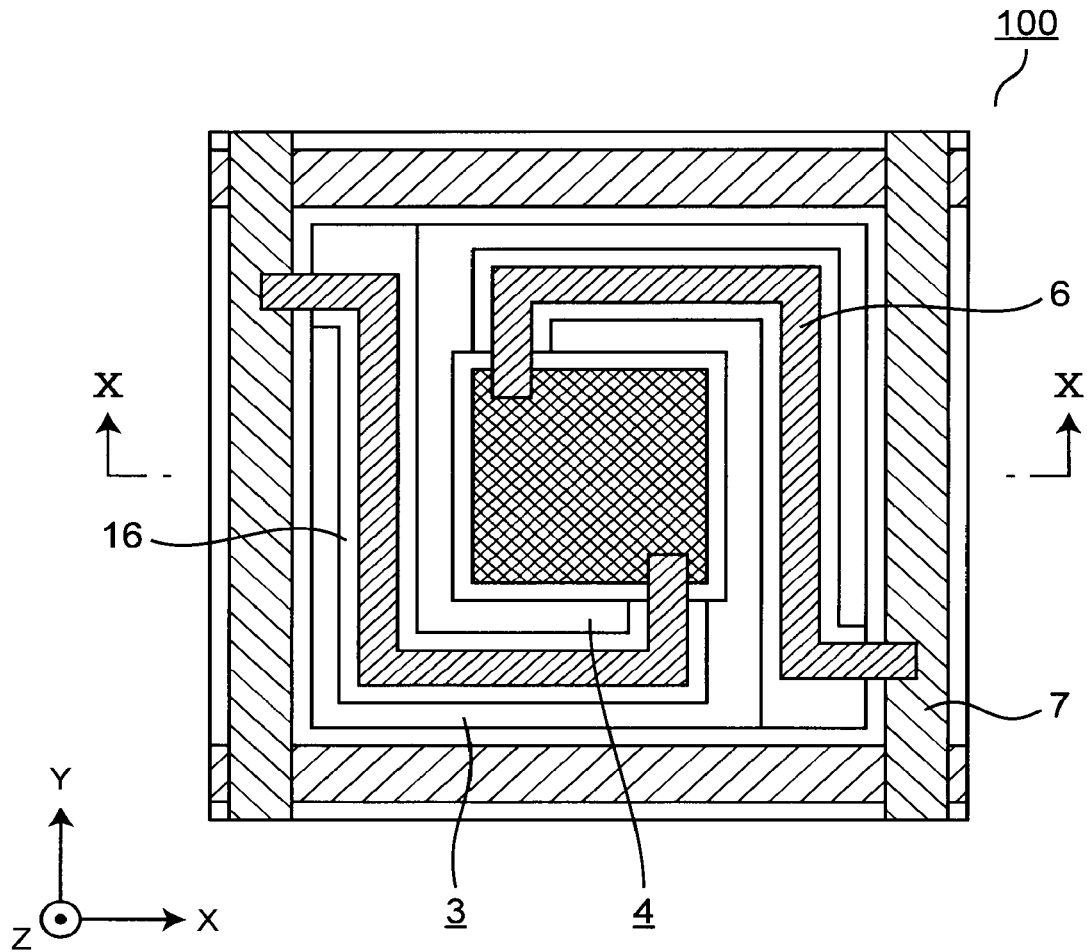
FIG. 12 is a top view of an optical element of the infrared light detector of the non-invasive blood sugar level measurement device according to the first embodiment of the present invention.
Figure 13:
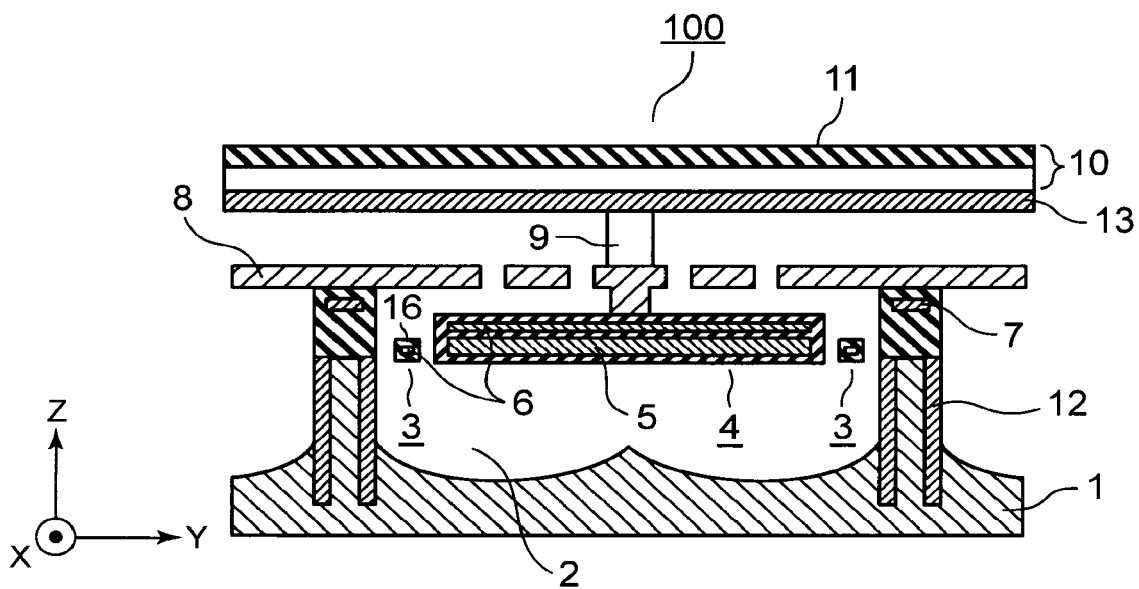
FIG. 13 is a cross-sectional view of the optical element of FIG. 12 as viewed in a direction X-X.

FIG. 12 is a top view of the optical element 100. In FIG. 12, a protective film on a wiring, a reflective film, and an absorber described later are omitted so as to clearly show the structure of the optical element 100. FIG. 13 is a cross-sectional view of the optical element 100 of FIG. 12 as viewed in a direction X-X. FIG. 13 shows an absorber 10 without omission.

As shown in FIG. 13, a hollow part 2 is disposed on the substrate 1. A temperature detection part 4 detecting a temperature is arranged above the hollow part 2. The temperature detection part 4 is supported by two support legs 3. As shown in FIG. 2, the support legs 3 have a bridge shape bent into an L-shape when viewed from above. The support legs 3 include a thin-film metal wiring 6 and a dielectric film 16 supporting the thin-film metal wiring 6.

The temperature detection part 4 includes a detection film 5 and the thin-film metal wiring 6. The detection film 5 is made of a diode using crystalline silicon, for example, and has a value of electric resistance changing depending on a temperature. The thin-film metal wiring 6 electrically connects an aluminum wiring 7 covered with an insulating film 12 to the detection film 5. The thin-film metal wiring 6 is made of a titanium alloy having a thickness of about 100 nm, for example. An electric signal output by the detection film 5 is transmitted to the aluminum wiring 7 via the thin-film metal wiring 6 formed on the support leg 3 and is taken out by the detection circuit 1010 (FIG. 11). The electric connections between the thin-film metal wiring 6 and the detection film 5 and between the thin-film metal wiring 6 and the aluminum wiring 7 are achieved via conductors (not shown) extending in a vertical direction as needed.

A reflection film 8 reflecting infrared rays is arranged to cover the hollow part 2. However, the reflection film 8 and the temperature detection part 4 are not thermally connected. The reflection film 8 is arranged to cover above at least a portion of the support legs 3.

A support column 9 is disposed above the temperature detection part 4 and supports the absorber 10 thereon. Therefore, the absorber 10 is thermally connected to the temperature detection part 4 by the support column 9. Thus, a temperature change generated in the absorber 10 is transmitted to the temperature detection part 4. On a back surface, i.e., on the support column 9 side, of the absorber 10, an absorption prevention film 13 preventing light absorption from the back surface is disposed. A metal film described later (a metal film 42 of FIG. 14) is disposed on a surface of the absorber 10 and is not shown in FIG. 13.

Figure 14:
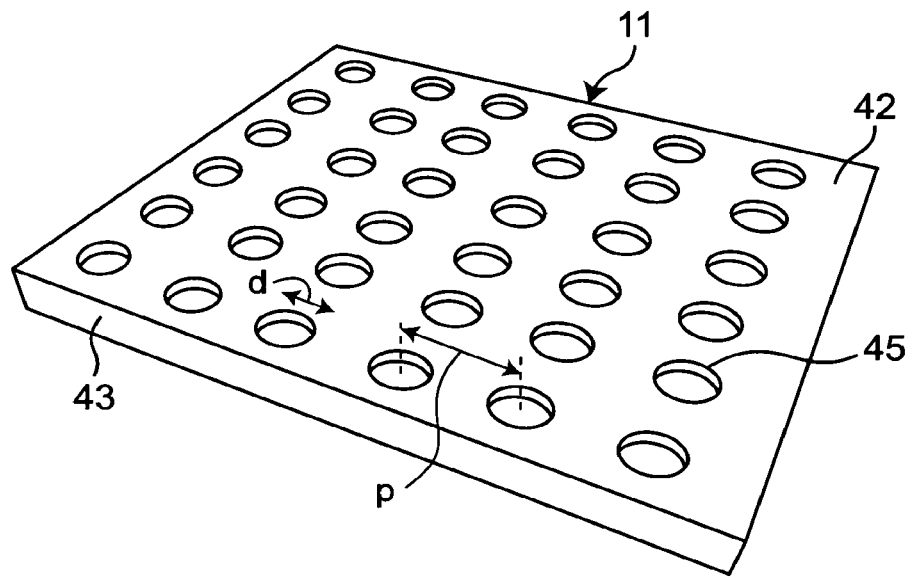
FIG. 14 is a perspective view showing an absorber of the optical element of the infrared light detector of the non-invasive blood sugar level measurement device according to the first embodiment of the present invention.

On the other hand, the absorber 10 is disposed above the reflective film 8 and is not thermally connected to the reflective film 8. The absorber 10 extends in a plate shape laterally (in a direction X-Y) so as to cover at least a portion of the reflection film 8. Therefore, as shown in FIG. 14 described later, when the optical element 100 is viewed from above, only the absorber 10 is visible. In another form, the absorber 10 may be formed directly on the temperature detection part 4.

FIG. 14 is a perspective view showing the absorber 10 of the optical element 100. The absorber 10 includes on a surface thereof a wavelength selection structural part 11 selectively absorbing a light having a specific wavelength. Since the wavelength selection structural part 11 may also absorb light, the wavelength selection structural part 11 is included in the absorber 10.

The optical element 100 utilizes surface plasmon in the wavelength selection structural part 11. When a periodic structure made of metal is disposed on an incidence plane of light, and a light having a wavelength corresponding to the surface periodic structure is made incident, surface plasmon occurs, and the light is absorbed. This can be utilized so that the wavelength of the light absorbed by the absorber 10 can be selected by making the surface of the absorber 10 from metal and adjusting the wavelength of the incident light, the incident angle, and a pitch p of the periodic structure of the metal surface.

In this description, when light is made incident, the generation of a surface mode to which free electrons inside a metal film contribute and the generation of a surface mode attributable to a periodic structure are considered to have the same meaning from the viewpoint of light absorption, and both are referred to as surface plasmon, surface plasmon resonance, or simply resonance without distinction. Additionally, the phenomena described above are sometimes referred to as pseudo surface plasmons or metamaterials; however, the phenomena are essentially the same in terms of absorption and are therefore not distinguished.

The wavelength selection structural part 11 includes a main body 43, a metal film 42 formed on the main body 43, and multiple concave parts 45 periodically disposed on the main body 43. The material of the metal film 42 is selected from metals such as Au, Ag, Cu, Al, Ni, or Mo causing the surface plasmon resonance. The material of the metal film 42 may be a metal nitride such as TiN, a metal boride, a metal carbide, etc. causing the surface plasmon resonance.

The thickness of the metal film 42 may be a thickness not allowing transmission of the incident light. This is because, when the thickness of the metal film 42 is such a thickness, only the surface plasmon resonance on the surface of the absorber 10 affects absorption and emission of electromagnetic waves, and the material under the metal film 42 does not have an optical influence on the absorption and emission. The thickness not allowing transmission of the incident light is related to a thickness of skin effect (skin depth) 61 represented by Eq. (10) below. Specifically, if the thickness of the metal film 42 is equal to or greater than twice of 51 (e.g., 10 nm to several hundred nm), almost no incident light passes through the metal film 42. Therefore, leakage of the incident light below the absorber 10 can sufficiently be reduced.

[Math. 10]

$$\delta = (2/\mu\sigma\omega)^{1/2} \quad (10)$$

where $\mu$ represents the magnetic permeability of the metal film 42, $\sigma$ represents the electric conductivity of the metal film 42, and $\omega$ represents the angular frequency of the incident light.

The main body 43 of the wavelength selection structural part 11 is made of a dielectric or a semiconductor. For example, the main body 43 of the wavelength selection structural part 11 is made of silicon oxide ($SiO_2$). The metal film 42 is made of gold, for example. Since the heat capacity of silicon oxide is smaller than the heat capacity of gold, the absorber 10 having the main body 43 made of silicon oxide and the metal film 42 made of gold has a smaller heat capacity as compared to an absorber made of only gold. As a result, the response of the optical element 100 can be made faster. Additionally, costs can be reduced as compared to an absorber made of only metal such as gold.

The concave parts 45 of the wavelength selection structural part 11 have a circular cylindrical shape with a diameter of 4 μm and a depth of 1.5 μm, for example. The wavelength selection structural part 11 has the circular cylindrical concave parts 45 arranged in a square lattice shape with a period (pitch) of 8 μm. In this case, the wavelength of the light absorbed by the absorber 10 is about 8 μm. The circular cylindrical concave parts 45 may be arranged in a square lattice shape at a period of 8.5 μm. In this case, the wavelength of the light absorbed by the absorber 10 is about 8.5 μm.

It was found that the relationships of the wavelength of the light absorbed by the absorber 10 (hereinafter, referred to as "absorption wavelength") and the wavelength of the light emitted from the absorber 10 (hereinafter referred to as "emission wavelength") with the period p of the concave parts 45 are substantially the same between when the concave parts 45 are arranged in a square lattice shape and when the concave parts 45 have a two-dimensional periodic structure other than the square lattice shape. In other words, in either case, the absorption wavelength and the emission wavelength are determined by the period p of the concave parts 45.

In this regard, theoretically, considering a reciprocal lattice vector of the periodic structure, it may be considered that, while the absorption wavelength and the emission wavelength are substantially equal to the period p in square lattice arrangement, the absorption wavelength and the emission wavelength are a period p×√3/2 in triangular lattice arrangement. However, actually, since the absorption wavelength and the emission wavelength slightly change depending on a diameter d of the concave part 45, a light having a wavelength substantially equal to the period p is considered to be absorbed or emitted in any two-dimensional periodic structure.

Therefore, the arrangement of the concave parts 45 is not limited to the square lattice and may be a two-dimensional periodic structure other than the square lattice such as a triangular lattice.

As described above, the wavelength of the light absorbed by the absorber 10 can be controlled by adjusting the period p of the concave parts 45. Generally, the diameter d of the concave part 45 is desirably equal to or greater than ½ of the period p. When the diameter d of the concave part 45 is smaller than ½ of the period p, the resonance effect is reduced, and the absorptance of the incident light tends to decrease. However, since the resonance is three-dimensional resonance in the concave parts 45, sufficient absorption may be achieved in some cases even if the diameter d is smaller than ½ of the period p. Therefore, the value of the diameter d relative to the period p may individually be designed as appropriate. What is important is that the absorption wavelength is determined mainly based on the period p and can therefore be controlled by adjusting the period p. If the diameter d is equal to or greater than a certain value relative to the period p, the absorber 10 has sufficient absorption characteristics. Therefore, the design conditions of the absorber can flexibly be determined.

On the other hand, it is known from the dispersion relationship of the surface plasmon that the light absorbed by the absorber 10 is independent of the depth of the concave parts 45 and depends only on the period p.

The absorber 10 including the periodically arranged concave parts 45 has been described. However, the wavelength selection structural part 11 of the absorber 10 may include periodically arranged convex parts protruding from the surface. Such a configuration has the same effects as described above.

In the above description, the concave parts 45 have a circular cylindrical shape; however, for example, the shape of the concave part 45 as viewed from above may be rectangular or elliptical. The arrangement of the concave parts 45 is not limited to the two-dimensional periodic arrangement and may be one-dimensional periodic arrangement, for example. In these cases, the absorption of the incident light depends on polarization of the incident light. For example, when the light emitted from the light source has a polarized light, the absorber 10 capable of absorbing only the polarized light can be designed. As a result, the SN ratio can be improved.

The absorption of the incident light by the absorber 10 is maximized when the incident light is perpendicularly incident on the absorber. If the angle of incidence on the absorber 10 deviates from being perpendicular, the absorption wavelength changes, and the absorptance of the incident light decreases.

A method of manufacturing the absorber 10 will be described. The periodic concave parts 45 are formed on the surface of the main body 43 made of a dielectric or a semiconductor by photolithography and dry etching. Subsequently, the metal film 42 is formed on the entire surface of the main body 43 including the concave part 45 by sputtering etc. Similarly, the metal film 42 is formed on the back surface. Since the diameter d of the concave parts 45 illustrated in the figure is as small as about several µm, the process of forming the metal film 42 after forming the concave parts 45 by etching the main body 43 is easier to perform than the process of forming the concave parts by directly etching the metal film 42.

Second Embodiment

Figure 15:
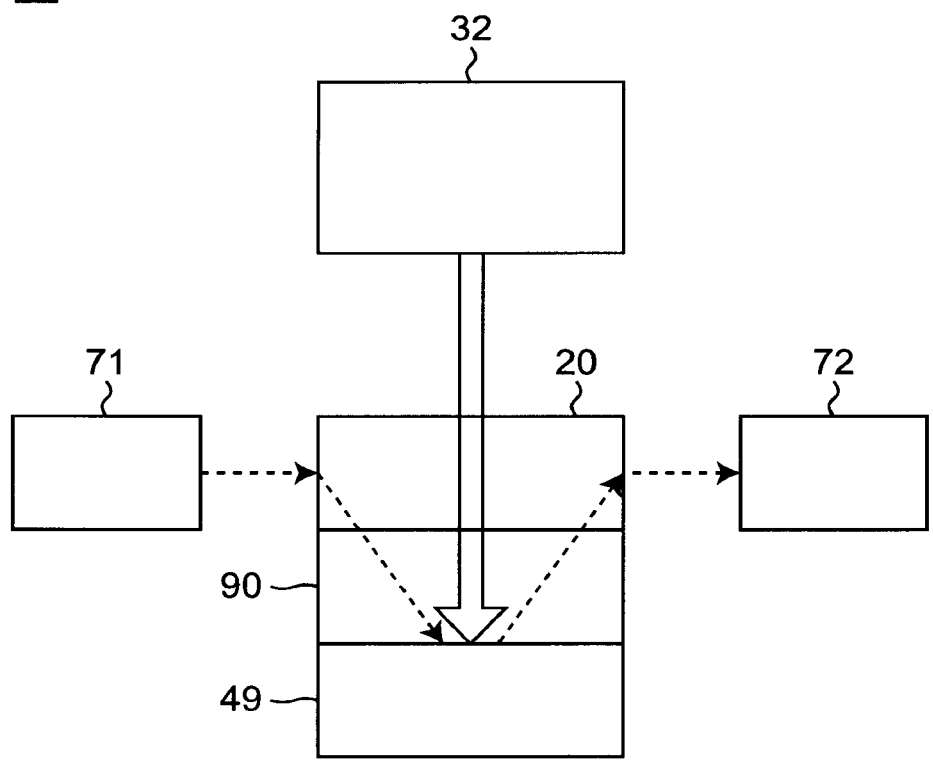
FIG. 15 is a schematic diagram showing a configuration of a non-invasive blood sugar level measurement device according to a second embodiment of the present invention.

FIG. 15 is a schematic diagram showing a configuration of a non-invasive blood sugar level measurement device denoted by 81 according to the second embodiment of the present invention. The non-invasive blood sugar level measurement device 81 includes the infrared light source 32 emitting an infrared light having a whole or a part of an absorption wavelength region of a biological material (8.5 µm to 10 µm), the ATR prism 20 through which the infrared light emitted from the infrared light source 32 is transmitted, and the hyperbolic metamaterial 90 formed on the ATR prism 20, a controller not shown, and a user interface not shown. FIG. 15 is a diagram during use, and the hyperbolic metamaterial 90 on a head of the non-invasive blood sugar level measurement device 81 is in contact with the skin 49 of the subject.

The non-invasive blood sugar level measurement device 81 according to the second embodiment of the present invention includes a visible light source 71 emitting a visible light toward the ATR prism 20, and a visible light detector 72 detecting the intensity and position of the visible light transmitted and emitted through the ATR prism 20.

The visible light emitted from the visible light source 71 is incident on the ATR prism 20. The incident visible light is transmitted through the ATR prism 20 while being repeatedly totally reflected, is subsequently emitted from the ATR prism 20, and enters the visible light detector 72.

The infrared light emitted from the infrared light source 32 reaches the skin 49 of the subject via the ATR prism 20 and the hyperbolic metamaterial 90. The infrared light is absorbed by a biological material (e.g., glucose) in the skin 49, thereby generating heat. The temperature of the ATR prism 20 increases due to the generated heat. As the temperature increases, an optical constant such as a refractive index of the ATR prism 20 changes, and the emission angle of the visible light emitted from the ATR prism 20 changes. The change in the emission angle changes a position where the visible light reaches. Therefore, the change in the optical constant of the ATR prism 20, and thus, the generated heat, can be determined by the visible light detector 72 detecting the position where the visible light reaches. Specifically, when the amount of the biological material is larger, the absorbed amount of the visible light becomes larger, and when the absorbed amount is larger, the generated heat more increases. Therefore, when the amount of the biological material is larger, the change in the emission angle of the visible light emitted from the ATR prism 20 becomes larger. In this way, the amount of the biological material in the skin 49 can be determined.

When the optical element of the visible light detector 72 has a single pixel, the reaching position of the emitted light can be specified by mechanical scanning, and the change in the emission angle of the visible light from the ATR prism 20 can be calculated.

As described above, the amount of the biological material can be determined by using the heat generated by absorbing the infrared light. This method is referred to as a light/heat method.

In such a measurement device, by forming the hyperbolic metamaterial 90 on the ATR prism 20, the change in the emission angle of the visible light from the ATR prism 20 can further be increased. When the hyperbolic metamaterial 90 is disposed on the ATR prism 20, the visible light incident on the ATR prism 20 and/or the evanescent wave generated by total reflection of the visible light at the interface between the ATR prism 20 and the hyperbolic metamaterial 90 passes through the hyperbolic metamaterial 90. An optical constant such as a refractive index of the hyperbolic metamaterial 90 changes due to temperature. Particularly, when the hyperbolic metamaterial 90 is used, the change in the emission angle of the visible light has greater temperature dependence as compared to when a material having an ordinary dispersion relationship is used. Therefore, by using the hyperbolic metamaterial 90, the emission angle of the visible light can further significantly be changed. Therefore, even if an amount of the visible light absorbed by the biological material is slight, the change in the emission angle can be made larger, so that the measurement accuracy is improved.

First Modification

Figure 16:
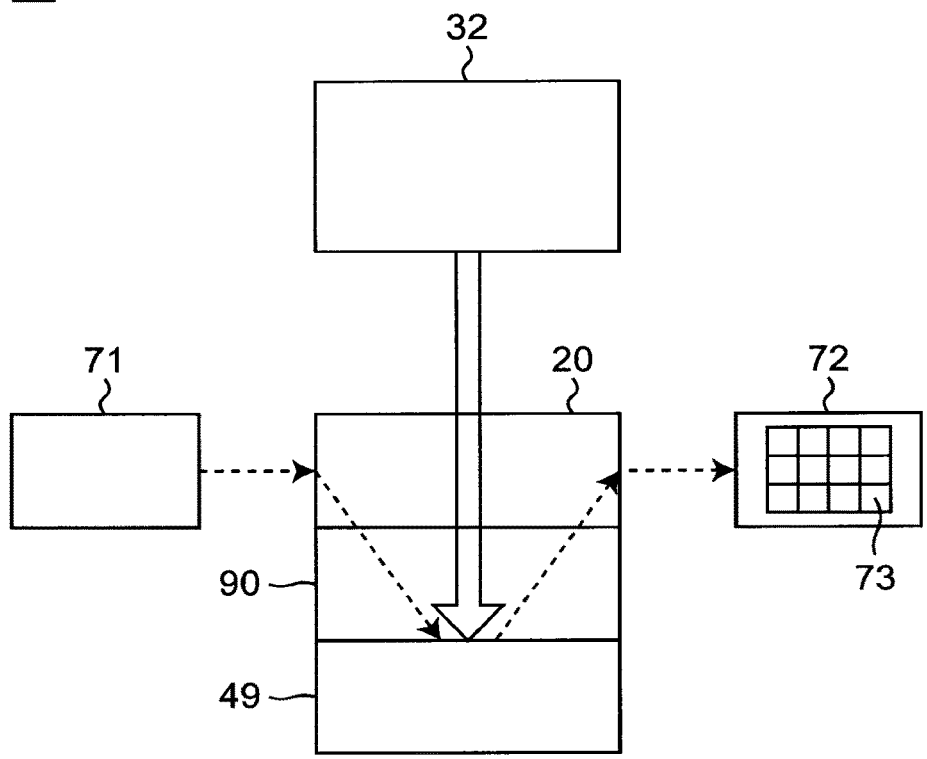
FIG. 16 is a schematic diagram showing a configuration of a non-invasive blood sugar level measurement device according to a first modification of the second embodiment of the present invention.

FIG. 16 is a schematic diagram showing a configuration of a non-invasive blood sugar level measurement device generally denoted by 82 according to a first modification of the second embodiment of the present invention. In the first modification of the second embodiment of the present invention, the visible light detector 72 includes multiple pixels (semiconductor optical elements) 73 arranged in a matrix shape (an array shape) in two directions orthogonal to each other.

By forming the visible light detector 72 as an array, an intensity of visible light can be detected for each of the pixels 73. Therefore, a position with the largest amount of visible light can finely be specified. As a result, the emission angle of the visible light from the ATR prism 20 can accurately be detected. Therefore, an amount of generated heat, i.e., an amount of the biological material, can accurately be measured from an amount of change in the emission angle.

Although FIG. 16 shows the twelve pixels 73, the number of the pixels 73 is not limited thereto. The visible light detector 72 may be an image sensor.

Second Modification

Figure 17:
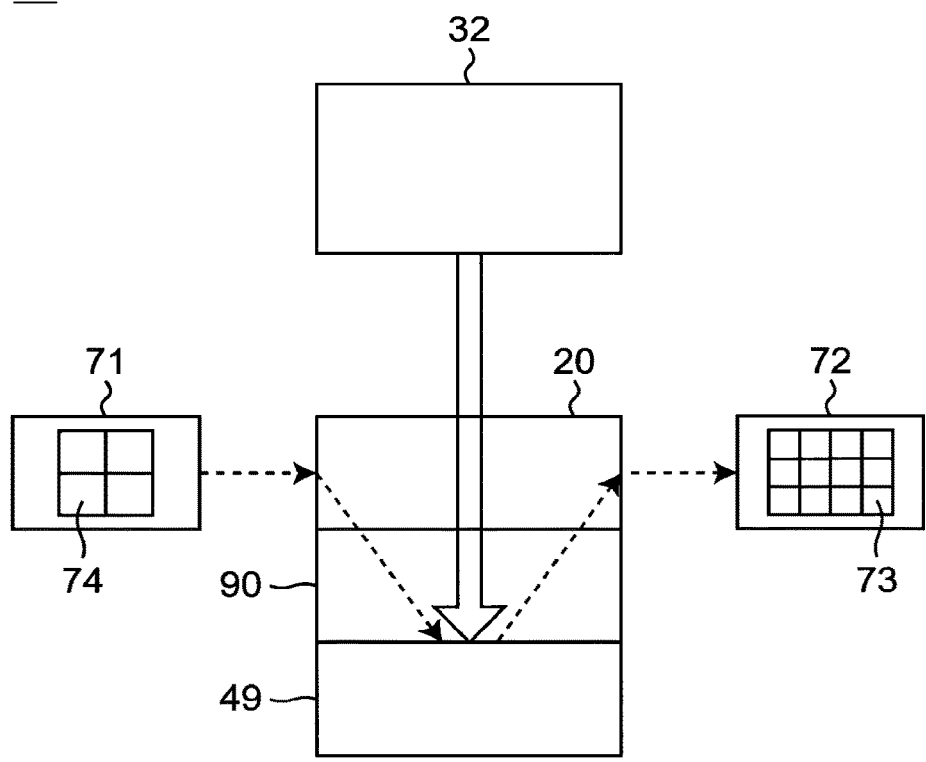
FIG. 17 is a schematic diagram showing a configuration of a non-invasive blood sugar level measurement device according to a second modification of the second embodiment of the present invention.

FIG. 17 is a schematic diagram showing a configuration of a non-invasive blood sugar level measurement device generally denoted by 83 according to a second modification of the second embodiment of the present invention. In the second modification of the second embodiment of the present invention, the visible light source 71 includes multiple light source elements 74 arranged in a matrix shape (an array shape) in two directions orthogonal to each other.

The multiple light source elements 74 may emit visible lights having the same wavelength. Since the multiple light source elements 74 are arranged at different positions, the visible lights emitted from the light source elements 74 are incident on the ATR prism 20 at different positions or incident angles. Therefore, the visible lights emitted from the light source elements 74 are respectively incident at different positions on the skin 49. If the incident position on the skin 49 is different, the influence of the temperature is different, so that the changes in emission angle of the visible lights from the ATR prism 20 due to the temperature become different from each other. By calculating a change in the emission angle due to a difference in the incident position of the visible light, the measurement accuracy can be improved.

Unlike the above description, at least one of the multiple light source elements 74 may emit a visible light having a wavelength different from the other light source elements 74. By calculating a change in the emission angle due to a difference in the wavelength of the visible light, the measurement accuracy can be improved.

In the second modification of the second embodiment of the present invention, the emission angle of the visible light can further significantly be changed by using the hyperbolic metamaterial 90. Therefore, even if an amount of the visible light absorbed by the biological material is slight, the change in the emission angle can be made larger, so that the measurement accuracy is improved.

EXPLANATIONS OF LETTERS OR NUMERALS absorber, 11 wavelength selection structural part, 20 ATR prism, 30 infrared light detector, 32 infrared light source, controller, 54 user interface, 71 visible light source, visible light detector, 74 light source element, 80 non-invasive blood sugar level measurement device, 90 hyperbolic metamaterial, 91 metal layer, 92 dielectric layer, defect layer, 100 optical element, 1000 sensor array, 1010 detection circuit.

The invention claimed is:

1. A biological material measurement device comprising:
a first light source emitting a first light;
an ATR prism including a front surface and a back surface and allowing the first light made incident from one end to be transmitted therethrough and emitted from the other end;
a hyperbolic metamaterial layer including a front surface and a back surface and arranged on the front surface of the ATR prism such that the back surface of the hyperbolic metamaterial layer is in contact therewith; and
a first light detector detecting the first light emitted from the ATR prism, wherein
the hyperbolic metamaterial layer has a structure in which a plurality of metal layers containing metal and a plurality of dielectric layers are alternately laminated in a direction perpendicular to the front surface of the ATR prism, and wherein
an amount of a biological material in a living body is measured from the detected first light.

2. The biological material measurement device according to claim 1, wherein
the first light made incident on the ATR prism is reflected by the back surface of the AIR prism as well as the front surface of the AIR prism and/or the front surface of the hyperbolic metamaterial layer and is transmitted through the ATR prism, and wherein
the hyperbolic metamaterial layer is brought into contact with a living body to measure the amount of the biological material in the living body from the amount of the first light absorbed by the living body.

3. The biological material measurement device according to claim 1, wherein
the first light detector includes a plurality of concave parts or convex parts arranged on a surface thereof separately from each other in a constant period in one direction or in two directions intersecting each other and having at least surfaces made of metal, and wherein
the constant period is a period of surface plasmon generated in the concave parts or the convex parts due to the incidence of the first light.

4. The biological material measurement device according to claim 1, wherein
the first light source, the ATR prism, the first light detector, and the hyperbolic metamaterial layer are arranged such that the first light emitted from the ATR prism is perpendicularly incident on the surface of the first light detector.

5. The biological material measurement device according to claim 1, wherein the first light is an infrared light.

6. The biological material measurement device according to claim 1, further comprising
a second light source emitting a second light, wherein
the first light made incident on the ATR prism is reflected by the back surface of the ATR prism as well as the front surface of the ATR prism and/or the front surface of the hyperbolic metamaterial layer and is transmitted through the ATR prism, and wherein
while the hyperbolic metamaterial layer is in contact with a living body, the second light is applied to the living body to measure the amount of the biological material from a change in the first light due to a heat generated by the biological material in the living body absorbing the second light.

7. The biological material measurement device according to claim 6, wherein the change in the first light is a change in an emission angle of the first light attributable to a change in a refractive index of the ATR prism and/or the hyperbolic metamaterial layer due to the heat.

8. The biological material measurement device according to claim 6, wherein
the first light detector includes a plurality of light detectors arranged at different positions, and wherein the amount of the biological material is calculated by using an intensity of the first light at each of the different positions and position data.

9. The biological material measurement device according to claim 6, wherein
the first light is a visible light, and wherein the second light is an infrared light.

10. The biological material measurement device according to claim 6, wherein the first light source includes a plurality of light sources emitting first lights having wavelengths different from each other.

11. The biological material measurement device according to claim 1, wherein the number of layers, thickness, and materials of the hyperbolic metamaterial layer are determined such that surface plasmon resonance occurs when the first light is made incident on the hyperbolic metamaterial layer.

12. The biological material measurement device according to claim 1, wherein the number of layers, thickness, and materials of the hyperbolic metamaterial layer are determined such that an optical constant of the hyperbolic metamaterial layer changes due to a temperature change.

13. The biological material measurement device according to claim 1, wherein a thickness of each of the metal layers and/or a thickness of each of the dielectric layers of the hyperbolic metamaterial layer is smaller than ¼ of the wavelength of the first light.

14. The biological material measurement device according to claim 1, wherein at least one layer of the metal layers and the dielectric layers of the hyperbolic metamaterial layer has a thickness different from thicknesses of the other layers of the metal layers and the dielectric layers of the hyperbolic metamaterial, and wherein the thicknesses of the other layers are equal.

15. A biological material measurement device comprising:
a first light source emitting a first light;
an ATR prism including a front surface and a back surface and allowing the first light made incident from one end to be transmitted therethrough and emitted from the other end;
a hyperbolic metamaterial layer including a front surface and a back surface and arranged on the front surface of the AIR prism such that the back surface of the hyperbolic metamaterial layer is in contact therewith; and
a first light detector detecting the first light emitted from the ATR prism, wherein
the hyperbolic metamaterial layer includes metal rods containing a metal and having a columnar shape with a central axis defined in a thickness direction of the hyperbolic metamaterial layer, and a dielectric filling a space spreading in a radial direction perpendicular to the central axis around the metal rods, and wherein
an amount of a biological material in a living body is measured from the detected first light.

16. The biological material measurement device according to claim 15, wherein the metal rods of the hyperbolic metamaterial layer are one-dimensionally or two-dimensionally periodically arranged in the radial direction, and wherein a thickness, an arrangement period, and a material of the metal rods are determined such that surface plasmon resonance occurs when the first light is made incident on the hyperbolic metamaterial layer.

17. The biological material measurement device according to claim 15, wherein the metal rods of the hyperbolic metamaterial layer are one-dimensionally or two-dimensionally periodically arranged in the radial direction, and wherein a thickness, an arrangement period, and a material of the metal rods are determined such that an optical constant of the hyperbolic metamaterial layer changes due to a temperature change.

18. The biological material measurement device according to claim 15, wherein the thickness and/or the arrangement period of the metal rods of the hyperbolic metamaterial layer is smaller than ¼ of the wavelength of the first light.

19. The biological material measurement device according to claim 15, wherein at least one of the metal rods has a thickness different from thicknesses of the other metal rods.

20. The biological material measurement device according claim 1, wherein the metal includes graphene.

* * * * *